US010259009B2

(12) United States Patent
Kurosaki et al.

(10) Patent No.: US 10,259,009 B2
(45) Date of Patent: Apr. 16, 2019

(54) BALLOON COATING METHOD AND BALLOON COATING APPARATUS

(71) Applicant: TERUMO KABUSHIKI KAISHA, Shibuya-ku, Tokyo (JP)

(72) Inventors: Yasuo Kurosaki, Kanagawa (JP); Eisuke Furuichi, Kanagawa (JP); Hiroshi Goto, Kanagawa-ken (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 92 days.

(21) Appl. No.: 15/188,192

(22) Filed: Jun. 21, 2016

(65) Prior Publication Data
US 2016/0296969 A1    Oct. 13, 2016

Related U.S. Application Data

(63) Continuation of application No. PCT/JP2014/083645, filed on Dec. 19, 2014.

(30) Foreign Application Priority Data

Dec. 21, 2013 (JP) ................................ 2013-264709

(51) Int. Cl.
*B05D 3/00* (2006.01)
*B05D 1/00* (2006.01)
(Continued)

(52) U.S. Cl.
CPC ............ *B05D 3/007* (2013.01); *A61K 31/337* (2013.01); *A61L 29/08* (2013.01); *A61L 29/16* (2013.01);
(Continued)

(58) Field of Classification Search
CPC .......... B05D 3/007; B05D 1/002; B05D 1/26; A61K 31/337; A61L 29/08; A61L 29/16;
(Continued)

(56) References Cited

U.S. PATENT DOCUMENTS

2010/0055294 A1   3/2010  Wang et al.
2011/0281020 A1   11/2011 Gong et al.
(Continued)

FOREIGN PATENT DOCUMENTS

WO   WO 2005/082550 A1     9/2005
WO   WO-2005082550 A1 *   9/2005   ............. G11B 7/266
WO   WO 2013/181498 A1    12/2013

OTHER PUBLICATIONS

*International Search Report (PCT/ISA/210) dated Feb. 10, 2015, by the Japanese Patent Office as the International Searching Authority for International Application No. PCT/JP2014/083645.
(Continued)

*Primary Examiner* — Andrew J Bowman
(74) *Attorney, Agent, or Firm* — Buchanan Ingersoll & Rooney PC

(57) ABSTRACT

A balloon coating method and a balloon coating apparatus are disclosed by which the thickness and/or morphological form of a drug in a coating formed on a balloon can be appropriately set. The balloon coating method can include moving a coating section for applying a coating liquid containing a drug relative to the balloon in the direction of an axis, while rotating the balloon about the axis of the balloon, thereby to apply the coating liquid to an outer surface of the balloon; detecting the distance of a dried part where the coating liquid applied to the outer surface of the balloon has been dried from the coating section; and controlling moving velocity of the coating section relative to the balloon in such a manner that the distance of the dried part from the coating section is maintained at a preliminarily set designated distance.

17 Claims, 16 Drawing Sheets

(51) Int. Cl.
  *B05D 1/26* (2006.01)
  *A61M 25/10* (2013.01)
  *B05C 11/10* (2006.01)
  *B05C 13/02* (2006.01)
  *A61K 31/337* (2006.01)
  *A61L 29/08* (2006.01)
  *A61L 29/16* (2006.01)
  *B05C 5/02* (2006.01)

(52) U.S. Cl.
  CPC ........ *A61M 25/10* (2013.01); *A61M 25/1029* (2013.01); *B05C 11/1005* (2013.01); *B05C 13/025* (2013.01); *B05D 1/002* (2013.01); *B05D 1/26* (2013.01); *A61L 2300/416* (2013.01); *A61L 2420/02* (2013.01); *A61M 2025/105* (2013.01); *A61M 2025/1031* (2013.01); *A61M 2207/10* (2013.01); *B05C 5/02* (2013.01)

(58) Field of Classification Search
  CPC .............. A61M 25/10; A61M 25/1029; B05C 11/1005; B05C 13/025
  USPC ...................................................... 427/2.28
  See application file for complete search history.

(56) References Cited

U.S. PATENT DOCUMENTS

2012/0315374 A1* 12/2012 Nguyen .............. B05B 13/0442
                                                       427/2.28
2013/0337147 A1* 12/2013 Chappa ............. A61M 25/1027
                                                        427/2.3

OTHER PUBLICATIONS

Notification of Reasons for Refusal dated Jul. 9, 2018, in corresponding Japanese Patent Application No. 2015-553613, and an English language machine translation thereof.
First Office Action dated Aug. 28, 2018, in corresponding Chinese Patent Application No. 201480069990.2, and an English language translation thereof.
Search Opinion dated Jul. 4, 2017, in corresponding European Patent Application No. 14 871 255.7.

* cited by examiner

BALLOON COATING METHOD AND BALLOON COATING APPARATUS

CROSS-REFERENCES TO RELATED APPLICATIONS

This application is a continuation of International Application No. PCT/JP2014/083645 filed on Dec. 19, 2014, and claims priority to Japanese Application No. 2013-264709 filed on Dec. 21, 2013, the entire content of both of which is incorporated herein by reference.

TECHNICAL FIELD

The present disclosure relates to a balloon coating method and a balloon coating apparatus for forming a coating layer on a surface of a balloon.

BACKGROUND ART

In recent years, balloon catheters have been used for improving lesion affected areas (stenosed parts) generated in body lumens. A balloon catheter can include an elongate shaft portion, and a balloon, which is provided on the distal side of the shaft portion and is inflatable in the radial direction. After the balloon in a deflated state is brought to a target site in the body by way of a thin body lumen, the balloon is inflated, whereby the lesion affected area can be pushed wide open.

If a lesion affected area is forcibly pushed open, excessive proliferation of endothelial cells may occur, causing new stenosis (restenosis). In view of this, recently, drug eluting balloons wherein an outer surface of a balloon is coated with a drug for restraining stenosis have been used. The drug eluting balloon, by being inflated, is able to instantaneously release the drug contained in the coating on the outer surface thereof to the lesion affected area and transfer the drug to the living body tissue, thereby restraining restenosis.

A variety of methods have been proposed for coating a balloon with a drug. For instance, U.S. Patent Application Publication No. 2010/055294 describes a method in which a coating liquid containing a drug is supplied to a surface of a balloon while the coating quantity is being controlled and the balloon is being rotated and being moved in an axial direction, and the coating liquid is dried to form a coating layer containing the drug.

SUMMARY

The drug in the coating formed on the outer surface of the balloon can assume different morphological forms such as crystalline form, amorphous form and mixed forms thereof depending on the length of time of volatilization of the solvent, etc. Neither of the crystalline form and the amorphous form is more desirable than the other, and it can be desirable that the morphological form of the drug can be selected according to the purpose.

A balloon coating method and balloon coating apparatus are disclosed by which, for example, the thickness and/or morphological form of a drug in a coating formed on a balloon can be appropriately set.

A balloon coating method is disclosed for forming a coating layer on an outer surface of a balloon of a balloon catheter, the method including: a coating step of moving a coating section relative to the balloon in an axial direction of the balloon for applying a coating liquid containing a drug, while rotating the balloon about an axis, thereby to apply the coating liquid to an outer surface of the balloon; a detection step of detecting the distance of a dried part where the coating liquid applied to the outer surface of the balloon has been dried from the coating section; and a control step of controlling moving velocity of the coating section relative to the balloon in such a manner that the distance of the dried part from the coating section is maintained at a preliminarily set designated distance.

In the balloon coating method configured as above, the moving velocity of the coating section relative to the balloon is controlled in such a manner that the distance of the dried part from the coating section will be maintained at the designated distance. Therefore, the distance of the coating section from the dried part can be constantly maintained in the state of being spaced by an appropriate distance, so that, for example, the thickness and/or morphological form of the drug in the coating formed on the balloon can be appropriately set.

In the control step, rotational speed of the balloon and quantity of the coating liquid ejected from the coating section per unit time are controlled according to variation in moving velocity of the coating section in such a manner that the quantity of the coating liquid applied to the balloon surface per unit time will be equal to a preliminarily set value, the coating quantity of the coating liquid can be uniform, even if the moving velocity varies, and a coating layer can be formed having a uniform thickness.

In the control step, the rotational speed of the balloon can be controlled in such a manner that the rotational speed will be equal to a value obtained by dividing the changed moving velocity of the coating section by a coating width along the axial direction by which the coating liquid is applied at a time by the coating section, the position where the coating liquid is applied onto the balloon by the coating section is moved by the coating width of the coating section per one revolution of the balloon. Therefore, two-time (or twice) coating of the balloon does not occur, and no gap is generated between portions of the coating liquid applied in a spiral pattern. Accordingly, the coating liquid can be applied without wasting the coating liquid and in a uniform thickness.

In the detection step, the position of the dried part on the outer surface of the balloon is detected from a radially outer side of the balloon, such that the distance from the coating section to the dried part can be calculated.

In the detection step, the position of the dried part on the outer surface of the balloon is detected from a radially outer side of the balloon by use of the detection section moved together with the coating section, the distance from the coating section to the dried part is detected directly without taking into account the movement of the coating section. Accordingly, the distance can be calculated relatively easily and accurately.

The balloon coating method may have a configuration wherein in the detection step, detection of the undried part where the coating liquid has not yet been dried is performed on a side nearer to the coating section than a reference position spaced by a designated distance from the coating section, by a first detection section moved together with the coating section, whereas detection of the dried part is performed on a side farther from the coating section than the reference position, by a second detection section moved together with the coating section; and in the control step, the moving velocity of the coating section is not changed in a case where the undried part is detected by the first detection section and the dried part is detected by the second detection section, the moving velocity of the coating section is increased in a case where the undried part is not detected by the first detection section, and the moving velocity of the coating section is lowered in a case where the dried part is not detected by the second detection section. When this configuration is adopted, the distance from the coating section to the dried part can be detected by only determining whether or not a part under consideration is the undried part by the first detection section and determining whether or not a part under consideration is the dried part by the second detection section, with the first detection part and the second detection part being moved together with the coating section. Thus, control can be easily realized.

In the detection step, a control is conducted such that the width along the axial direction of the undried part detected by the first detection section will be in the range of 2 mm to 20 mm, and, for example, the thickness and/or morphological form of the drug in the coating formed on the balloon can be appropriately set.

In the detection step, a control is conducted such that the length from an allowable upper limit to an allowable lower limit of the width along the axial direction of the undried part detected by the first detection section will be not more than 12 mm during a period from start of coating to end of coating, and, for example, the thickness and/or morphological form of the drug in the coating formed on the balloon can be appropriately set.

Where a sensor for detecting transmittance of light is used as the detection section, the dried part of the coating liquid can be relatively easily identified by utilizing transmittance that varies due to the dried part of the coating liquid.

Where a color difference meter is used as the detection section, the dried part of the coating liquid can be relatively easily identified by utilizing color that changes due to the dried part of the coating liquid.

A balloon coating apparatus is disclosed for forming a coating layer on an outer surface of a balloon of a balloon catheter can include: a rotating mechanism configured to rotate the balloon about an axis of the balloon; a coating mechanism configured to apply a coating liquid containing a drug to the outer surface of the balloon by moving relative to the balloon in an axial direction of the balloon; a detection section configured to detect a dried part where the coating liquid applied to the outer surface of the balloon has been dried; and a control unit configured to control moving velocity of the coating section relative to the balloon in such a manner that the distance of the dried part from the coating section is maintained at a preliminarily set designated distance. According to this configuration, the distance of the coating section from the dried part can be constantly maintained in the state of being spaced by an appropriate distance, so that, for example, the thickness and/or morphological form of the drug in the coating formed on the balloon can be appropriately set.

A balloon coating method is disclosed for forming a coating layer on an outer surface of a balloon of a balloon catheter, the method comprising: rotating the balloon about an axis of the balloon; applying a coating liquid containing a drug to an outer surface of the balloon by moving a coating section relative to the balloon in an axial direction; detecting a distance of a dried part where the coating liquid applied to the outer surface of the balloon has been dried from the coating section; and controlling a moving velocity of the coating section relative to the balloon and maintaining the distance of the dried part from the coating section at a preliminarily set designated distance.

DESCRIPTION OF EMBODIMENTS

Figure 1:
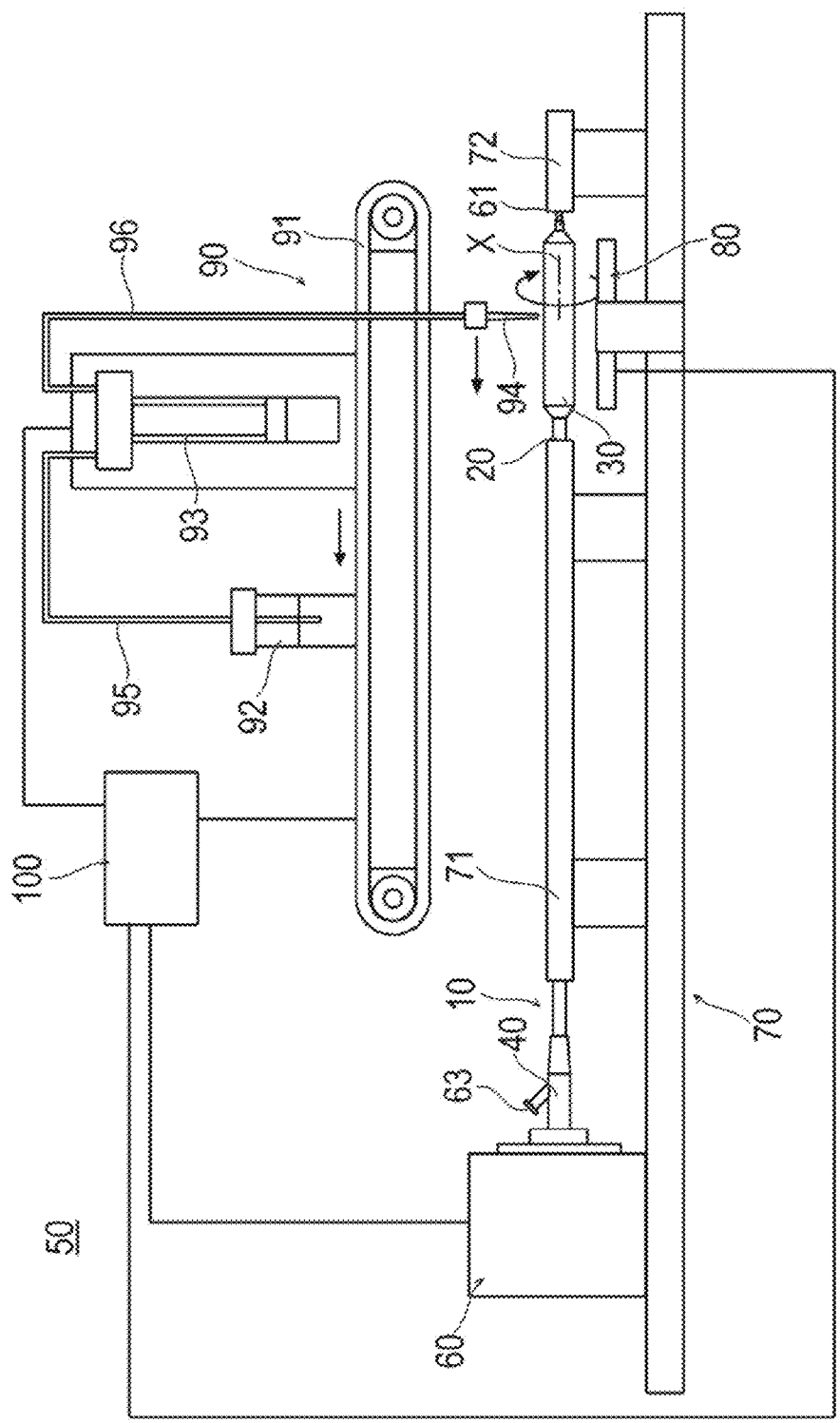
FIG. 1 is a schematic view showing an apparatus for carrying out a balloon coating method according to a first embodiment.

Embodiments of the present disclosure will be described below, referring to the drawings. Note that the dimensional ratios in the drawings may be exaggerated for convenience of explanation and may therefore be different from the actual ratios.

A balloon coating method according to a first embodiment of the present disclosure is for forming a coating layer containing a drug on a surface of a balloon, and is carried out by a balloon coating apparatus 50 illustrated in FIG. 1. Note that herein the side on which a balloon catheter 10 is inserted into a body lumen will be referred to as "distal end" or "distal side," and the side of an operator's hand operation will be referred to as "proximal end" or "proximal side."

Figure 2:
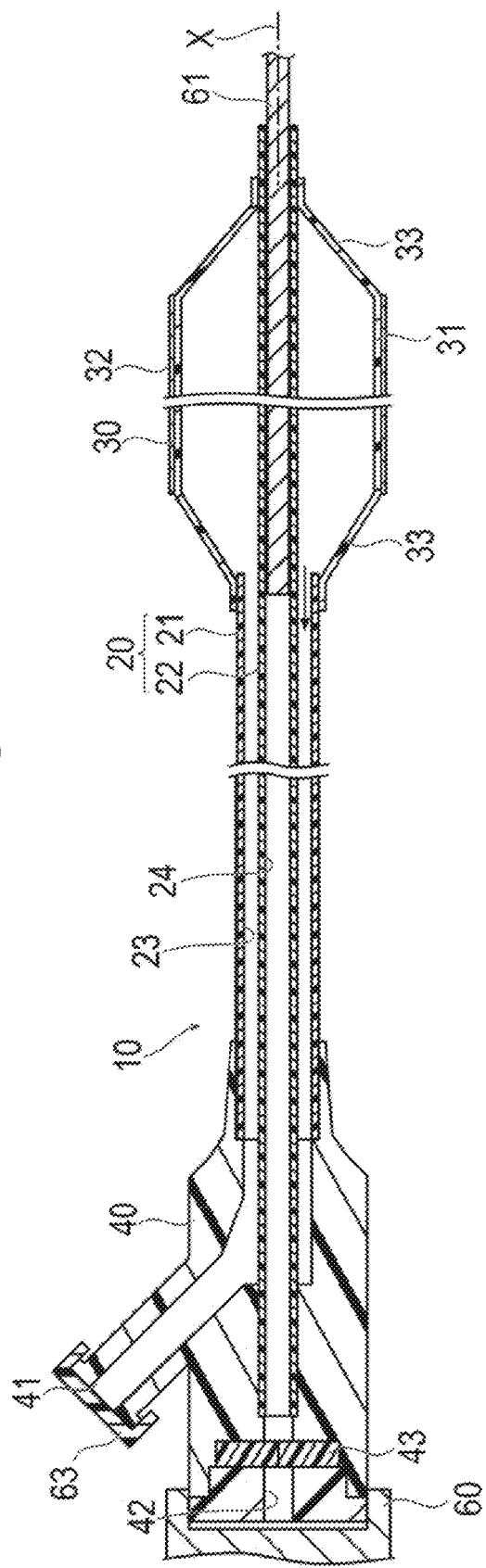
FIG. 2 is a sectional view showing a balloon catheter.

In accordance with an exemplary embodiment, the structure of the balloon catheter 10 will be described. As shown in FIG. 2, the balloon catheter 10 can include an elongate catheter main body section 20, a balloon 30 provided at a distal portion of the catheter main body section 20, and a hub 40 firmly attached to a proximal end of the catheter main body section 20.

The catheter main body section 20 can include an outer tube 21 which is a tube-shaped body opening at a distal end and a proximal end thereof, and an inner tube 22 disposed inside the outer tube 21. Between the outer tube 21 and the inner tube 22 is formed an inflation lumen 23 through which an inflation fluid for inflating the balloon 30 flows. Inside the inner tube 22 is formed a guide wire lumen 24 in and through which a guide wire can be inserted and passed.

The balloon 30 is adhered to the inner tube 22 on a distal side, and is adhered to the outer tube 21 on a proximal side, and the inside of the balloon 30 communicates with the inflation lumen 23. The balloon 30 is formed, at a central portion in the direction of an axis X thereof, with a cylindrical straight portion 31 having a constant outside diameter when inflated, and is formed, on both sides in the direction of the axis X of the straight portion 31, with tapered portions 33 which are gradually varied in outside diameter. A coating layer 32 containing a drug is formed on the whole part of an outer surface of the straight portion 31. Note that the range of formation of the coating layer 32 on the balloon 30 is not limited to only the straight potion 31 but may include at least part of the tapered portions 33 in addition to the straight portion 31, or may be only part of the straight portion 31.

The hub 40 can include a first opening portion 41 that functions as a port which communicates with the inflation lumen 23 of the outer tube 21 and through which the inflation fluid can flow in and out, and a second opening portion 42 in and through which the guide wire is inserted and passes through. A blood stop valve 43 for inhibiting blood from flowing out is provided at the second opening portion 42.

The balloon 30 is preferably formed from a material, which has a certain degree of flexibility. Examples of such a usable material can include thermoplastic resins such as polyolefins such as polyethylene, polypropylene, polybutene, ethylene-propylene copolymers, ethylene-vinyl acetate copolymers, ionomers, and mixtures of two or more of them, flexible polyvinyl chloride resin, polyamides, polyamide elastomers, polyesters, polyester elastomers, polyurethanes, fluororesins, silicone rubbers, and latex rubber.

The balloon coating apparatus 50 will be described next. As depicted in FIG. 1, the balloon coating apparatus 50 can include a rotating mechanism 60 for holding and rotating the balloon catheter 10 about the axis X of the balloon 30, a detection section 80 for detecting a coating liquid R applied to an outer surface of the balloon 30, a coating mechanism 90 for coating a surface of the balloon 30 with the coating liquid R, and a control mechanism 100 for controlling the balloon coating apparatus 50.

The rotating mechanism 60 holds the hub 40 of the balloon catheter 10, and rotates the balloon catheter 10 by a drive source, such as a motor, incorporated in balloon coating apparatus 50. The balloon catheter 10 has a core member 61 inserted and held in the guide wire lumen 24, such that the coating liquid R can be prevented from flowing into the guide wire lumen 24 by the core member 61. In addition, the balloon catheter 10 has a cap 63, which can be placed on the first opening portion 41 of the hub 40 in such a manner as to cover the inflation lumen 23, whereby the inflation fluid can be sealed when the balloon 30 is inflated.

A support base 70 can include a proximal-side support section 71 in which the catheter main body portion 20 is accommodated and supported in a rotatable manner, and a distal-side support section 72 by which a core member 61 is supported in a rotatable manner. Note that by the distal-side support portion 72, a distal portion of the catheter main body portion 20, instead of the core member 61, may be supported in a rotatable manner, if possible.

In accordance with an exemplary embodiment, the detection section 80 detects the position, on the balloon 30, of a dried part B (see the alternate long and two short dashes line in FIG. 3) where the coating liquid R applied to the outer surface of the balloon 30 has been dried through volatilization of the solvent and the drug has been precipitated. The detection section 80 is connected to the control unit 100, and transmits a detection signal to the control unit 100. The detection section 80 is capable of detecting at least a coated range of the balloon 30, over the whole part in the direction of the axis X, and detects the dried part B in terms of area or length along the direction of the axis X. When the coating liquid R is dried and the drug is precipitated, light transmittance or color is changed (for example, changed into a white color). Therefore, for example, a transmittance measuring sensor based on laser light, a color difference meter can be applied to the detection section 80. Alternatively, a camera can be used as the detection section 80, and the dried part B can be detected from an obtained image through image processing.

The coating mechanism 90 can include a movable base 91 movable rectilinearly in a direction parallel to the axis X of the balloon 30, a vessel 92 accommodating the coating liquid R, a liquid feed pump 93 for feeding the coating liquid R in an arbitrary feed quantity, and a coating section 94 for coating the balloon 30 with the coating liquid R.

The movable base 91 can be rectilinearly moved in both directions along the axis X of the balloon catheter 10, by a drive source such as a motor incorporated in the balloon coating apparatus 50.

The liquid feed pump 93 can be, for example, a syringe pump, which is controlled by the control mechanism 100.

The liquid feed pump 93 can be configured to suck the coating liquid R from the vessel 92 through a suction tube 95, and can supply the coating liquid R to the coating section 94 through a supply tube 96 in an arbitrary liquid feed quantity. The liquid feed pump 93 is disposed on the movable base 91, and can be moved rectilinearly by movement of the movable base 91. Note that the liquid feed pump 93 is not limited to the syringe pump so long as it can feed the coating liquid R; for example, it may be a tube pump.

The coating section 94 is a tubular dispensing tube which ejects the coating liquid R from an opening portion opening toward an outer surface of the balloon 30. The opening portion of the coating section 94 is formed to open in a plane orthogonal to an axis of the coating section 94, but this is not restrictive. The coating section 94 can be rectilinearly moved in both directions along the axis X of the balloon catheter 10, together with the liquid feed pump 93 disposed on the movable base 91. Note that the coating section 94 may not be the dispensing tube, so long as it can coat the outer surface of the balloon 30 with the coating liquid R; for example, the coating section 94 may be a porous body such as fibrous material, woven fabric, nonwoven fabric, sponge, impregnated with the coating liquid R, a spatula-like member, or a brush.

In accordance with an exemplary embodiment, the control mechanism 100 is composed, for example, of a computer, which receives a detection result signal from the detection section 80, and generally controls the rotating mechanism 60 and the coating mechanism 90.

The coating liquid R contains a drug, an additive or additives, and a volatile solvent. The drug is a substance, which can act on a living body, and may be either a water-soluble drug or a water-insoluble drug. From the viewpoint of restraining elution of the drug into blood, the drug is preferably a water-insoluble drug.

The water-insoluble drug means a drug which is insoluble or difficultly soluble in water; specifically, for example, the solubility of the drug in water is less than 5 mg/mL at pH 5 to 8. The solubility may be less than 1 mg/mL, or, further, may be less than 0.1 mg/mL. The water-insoluble drug can include, for example, fat-soluble drug.

Some examples of the preferred water-insoluble drug can include immunosuppressant, for example, cyclosporines inclusive of cyclosporine, immunoadjuvant such as rapamycin, carcinostatic agent such as paclitaxel, antiviral or antibacterial agent, antineoplastic agent, analgesic agent, antiinflammatory agent, antibiotic, antiepileptic, anxiolytic agent, antianesthetic agent, antagonist, neuron blocking agent, anticholinergic agent, antiarrhythmic agent, antihypertensive agent, hormone preparation, and nutritional supplement.

The water-insoluble drug is preferably at least one selected from rapamycin, paclitaxel, docetaxel, and everolimus. The rapamycin, paclitaxel, docetaxel and everolimus herein include their analogs and/or derivatives so long as the analogs and/or derivatives have equivalent drug activity to the original. For example, paclitaxel and docetaxel are in an analog relation. Rapamycin and everolimus are in a derivative relation. Among these, more preferable is paclitaxel.

The coating liquid R in this embodiment preferably contains the water-insoluble drug in a concentration, for example, of 5 mg/mL to 60 mg/mL, more preferably in a concentration of 20 mg/mL to 50 mg/mL, and further preferably in a concentration of 30 mg/mL to 40 mg/mL.

The additive is not particularly limited, and polymers and/or high molecular or low molecular compounds that form solid dispersion bodies with the drug are applicable. For example, the additive is preferably at least one selected from the group consisting of polyolefins, polyisobutylene, ethylene-α-olefin copolymer, acrylic polymers and copolymers, polyvinyl chloride, polyvinyl methyl ether, polyvinylidene fluoride, polyvinylidene chloride, polyacrylonitrile, polyvinyl ketone, polystyrene, polyvinyl acetate, ethylene-methyl methacrylate copolymer, acrylonitrile-styrene copolymer, ABS resin, nylon 12 and block copolymers thereof, polycaprolactone, polyoxymethylene, polyesters, polyethers, polyamides, epoxy resin, polyurethane, rayon triacetate, cellulose, cellulose acetate, cellulose butyrate, cellophane, cellulose nitrate, propionyl cellulose, cellulose ether, carboxymethyl cellulose, chitin, polylactic acid, polyglycolic acid, polyethylene oxide, polylactic acid-polyethylene oxide copolymer, polyethylene glycol, polypropylene glycol, glycerol, polyvinyl alcohol, polyvinyl pyrrolidone, organic acids, and organic acid esters. Note that the additive may not be provided.

The additive is preferably used in a small amount relative to the drug, and preferably does not form a matrix. In addition, the additive preferably does not include, but may include, micelles, liposome, contrast agent, emulsifier, or surfactant. In addition, the additive preferably can include only a low molecular compound or compounds, without including a polymer.

The volatile solvent is not specifically restricted, and preferably can include at least one of volatile organic solvents such as methanol, ethanol, dioxane, tetrahydrofuran, dimethyl formamide, acetonitrile, dimethyl sulfoxide, acetone, etc. Besides, the volatile organic solvent may be mixed with water or the like.

A balloon coating method for forming a coating layer 32 containing the drug on a surface of the balloon 30 by use of the aforementioned balloon coating apparatus 50 will be described below.

First, an inflation fluid is supplied via the first opening portion 41 of the balloon catheter 10 into the balloon 30 to inflate the balloon 30, and, in this condition, the first opening portion 41 is sealed by putting the cap 63 thereon, to thereby maintain the inflated state of the balloon 30. Note that the coating layer 32 can also be formed on the surface of the balloon 30 without inflating the balloon 30, in which case it is unnecessary to supply the inflation fluid into the balloon 30.

Next, the balloon catheter 10 is disposed on the support base 70 in a rotatable manner, and the hub 40 is interlocked to the rotating mechanism 60.

Subsequently, the movable base 91 is moved to locate the coating section 94 at a position on the distalmost side of a range where the coating layer 32 is to be formed on the balloon 30, for example, on the distalmost side of the straight portion 31, and the balloon catheter 10 is rotated by the rotating mechanism 60.

Next, the coating liquid R is supplied to the coating section 94 while the liquid feed quantity is regulated by the liquid feed pump 93 of the coating mechanism 90, and the movable base 91 is moved to gradually move the coating section 94 in the proximal direction (coating step). An initial value for the moving velocity Sx (mm/minute) of the coating section 94 is preliminarily inputted to the control unit 100. In addition, the rotational speed N (rpm) of the balloon 30 is calculated by the control unit 100 from the moving velocity Sx and the inside diameter D (mm) of a dispensing tube constituting the coating section 94 according to the following formula (1), and the rotating mechanism 60 is controlled by the control unit 100 such that the rotational speed N (rpm) will be equal to the calculated value. Note that the inside diameter D of the dispensing tube is also the coating width along the direction of the axis X by which the balloon 30 is coated at a time by the coating section 94.

$$N = Sx/D \quad \text{Formula (1)}$$

With the formula (1) satisfied, the position on the balloon 30 at which the coating section 94 applies the coating liquid R is moved by a length amount (coating width amount) of the inside diameter D per one revolution of the balloon 30. This can help ensure that two-time coating of the balloon 30 does not occur, and a gap is not generated between portions of the coating liquid R applied in a spiral pattern. Therefore, uniform coating with the coating liquid R can be achieved, without wasting the coating liquid R and while suppressing variability of the thickness of the coating liquid R applied. The moving velocity Sx of the coating section 94 is in the range of, for example, 3 mm/minute to 300 mm/minute, which is not limitative. The rotational speed N of the balloon 30 is in the range of, for example, 10 rpm to 300 rpm, which is not restrictive.

Ejection rate F (μL/minute) of the coating liquid R from the coating section 94 is calculated by the control unit 100 from the coating quantity V (μL/mm2) of the coating liquid R applied to the outer surface of the balloon 30 per unit area, the radius r (mm) of the balloon 30, the rotational speed N (rpm) calculated by the formula (1), and the inside diameter D (mm) of the dispensing tube according to the following formula (2), and the coating mechanism 90 is controlled by the control unit 100 such that the ejection rate F will be equal to the calculated value.

$$F = V \times 2\pi \times r \times N \times D \quad \text{Formula (2)}$$

With the ejection rate F controlled such as to satisfy the formula (2), the coating quantity V is maintained at a value which is preliminarily set as a desired value for the coating quantity on the balloon 30. The ejection rate F (μL/minute) of the coating liquid R is in the range of, for example, 3 μL/minute to 300 μL/minute, which is not limitative.

With the rotational speed N and the ejection rate F controlled in such a manner as to satisfy the formula (1) and the formula (2) as aforementioned, it is possible to suppress variability of the thickness of the coating liquid R and to make uniform the thickness of the coating layer 32 formed.

After the outer surface of the balloon 30 is coated with the coating liquid R, the volatile solvent contained in the coating liquid R volatilizes, whereby the coating liquid R is dried, and the coating layer 32 containing the drug and an additive or additives is gradually formed on the surface of the balloon 30. The time of volatilization is appropriately set according to the solvent, and, for example, can be several seconds to several tens of seconds.

Figure 3:
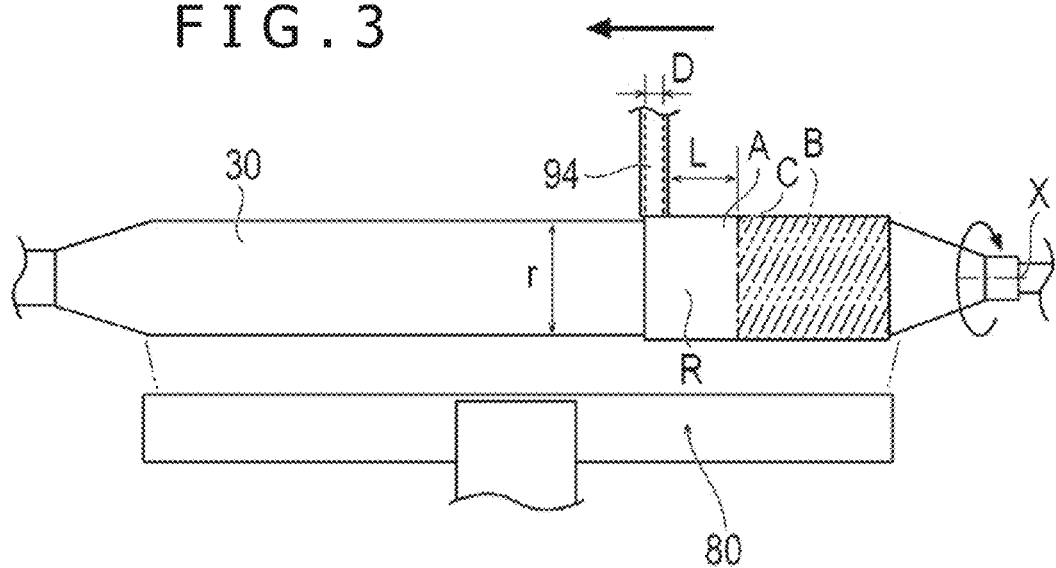
FIG. 3 is a plan view showing a balloon and a coating section in carrying out the balloon coating method according to the first embodiment.

Then, as the coating section 94 is moved proximally, as shown in FIG. 3, an undried part A where the coating liquid R has not yet been dried and a dried part B where the coating liquid R has been dried are formed on the distal side of the coating section 94, and the dried part B is detected by the detection section 80 (detection step). Between the undried part A and the dried part B is formed a drying boundary line C. At the time of detecting the dried part B, a value detected by the detection section 80 is compared with a preliminarily given threshold in the control unit 100, and a part where the detected value is not less than the threshold (or not more than the threshold) can be determined as the dried part B. The threshold can be set, for example, by preliminarily performing experiments. Note that the dried state may not necessarily be defined as a state where the solvent has volatilized strictly completely (100%).

Thereafter, on the basis of the signal received from the detection section 80, the moving velocity Sx of the coating section 94 relative to the balloon 30 is controlled in the control unit 100 in such a manner that the distance L of the dried part B from the coating section 94, or the distance L of the drying boundary line C from the coating section 94, will coincide with a designated distance L0, which is a fixed value or a value having a predetermined width (control step). Note that while the distance L of the dried part B from the coating section 94 is defined as the distance from an end surface of the coating section 94 on the side opposite to the moving direction to the drying boundary line C in FIG. 3, the distance L can also be defined as the width of the undried part A along the axial direction (undried distance). In the case where the designated distance L0 has a range, it is possible, for example, to set an upper limit and a lower limit, thereby defining the designated distance L0. In addition, in the case where the designated distance L0 has a range, it is possible to set a predetermined undried distance control value as a center value of the range and set an allowable fluctuation range in absolute value, thereby providing an allowable range corresponding to the allowable fluctuation range to the plus side and the minus side of the undried distance control value. In addition, it is also possible to set a predetermined undried distance control value as a set point in control, and to set different-valued allowable fluctuation ranges (absolute values) to the plus side and the minus side of the undried distance control value.

In order that the crystals assume a form including a plurality of elongate bodies having independent long axes, the width (the width along the axial direction) of the undried part A is, for example, desirably in the range of 2 mm to 20 mm in the case of a balloon 30 having a diameter of 7 mm, desirably in the range of 2 mm to 15 mm in the case of a balloon 30 having a diameter of 4 mm, and desirably in the range of 2 mm to 10 mm in the case of a balloon 30 having a diameter of 2 mm, the ranges being not limitative.

In addition, the length from an allowable upper limit to an allowable lower limit of the width of the undried part A from the start of coating to the end of coating is, for example, desirably not more than 12 mm in the case of a balloon 30 having a diameter of 7 mm, desirably not more than 10 mm in the case of a balloon 30 having a diameter of 4 mm, and desirably not more than 8 mm in the case of a balloon 30 having a diameter of 2 mm, the length values being not limitative.

In the case where a superficial femoral artery (SFA) of a lower limb is an object of treatment, a balloon 30 having a diameter of 4 mm to 7 mm is used. In view of this, the width of the undried part A is desirably in the range of, for example, 2 mm to 20 mm, and the length from an allowable upper limit to an allowable lower limit of the width of the undried part A from the start of coating to the end of coating is desirably, for example, not more than 12 mm. In the case where a below-the-knee artery (BTK) of a lower limb is an object of treatment, a balloon 30 having a diameter, for example, of 2 mm to 4 mm can be used. In view of this, the width of the undried part A is desirably in the range of, for example, 2 mm to 15 mm, and the length from an allowable upper limit to an allowable lower limit of the width of the undried part A from the start of coating to the end of coating is desirably, for example, not more than 10 mm.

In the case where a lower limb artery in general is an object of treatment, a balloon 30 having a diameter, for example, of 2 mm to 7 mm can be used. In view of this, the width of the undried part A is desirably in the range of, for example, 2 mm to 20 mm, and the length from an allowable upper limit to an allowable lower limit of the width of the undried part A from the start of coating to the end of coating is desirably, for example, not more than 12 mm.

Figure 4:
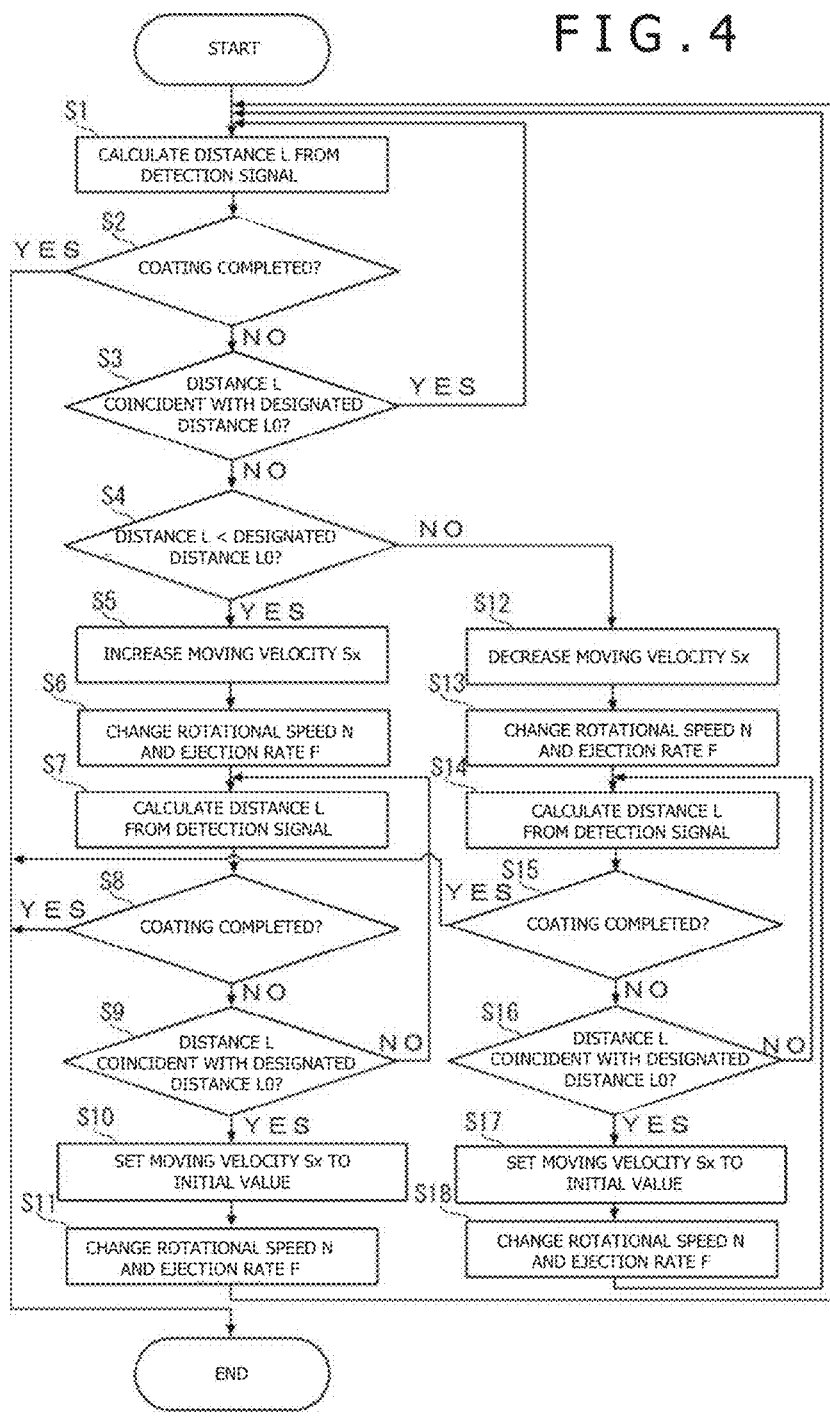
FIG. 4 is a flow chart showing a control flow in a control unit.

In the control step, as shown in a flow chart in FIG. 4, first, the dried part B is identified in the control unit 100 on the basis of a detection signal received from the detection section 80, and the distance L of the dried part B from the coating section 94 is calculated (step 1). Note that the position of the coating section 94 can be determined relatively easily from data in the control unit 100 without performing measurement, since the movable base 91 is controlled by the control unit 100.

Next, it is determined whether or not the distance L coincides with the preliminarily inputted designated distance L0 (step 3). If the distance L coincides with the preliminarily inputted designated distance L0, it is determined that the moving velocity Sx and the drying speed are kept appropriately, the moving velocity Sx is maintained unchanged, and step 1 is again executed.

If the distance L does not coincide with the preliminarily inputted designated distance L0, it is determined whether the distance L is in excess of the designated distance L0 or is less than the designated distance L0 (step 4). If the distance L is less than the preliminarily inputted designated distance L0, the moving velocity Sx of the coating section 94 is slower than the drying speed, and, accordingly, the movable base 91 of the coating mechanism 90 is controlled to increase the moving velocity Sx (step 5). The extent in which the moving velocity Sx is increased when the distance L is less than the designated distance L0 is preliminarily inputted as a parameter.

Thereafter, the rotational speed N of the balloon 30 and the ejection rate F of the coating liquid R are calculated according to the aforementioned formula (1) and formula (2), and the rotating mechanism 60 and the coating mechanism 90 are controlled by the control unit 100 such that the rotational speed N and the ejection rate F will be equal to the calculated values (step 6). After the moving velocity Sx is changed, the distance L is calculated on the basis of the signal from the detection section 80 (step 7), and it is determined whether or not the distance L coincides with the designated distance L0 (step 9). Then, the steps 7 to 9 are repeated until the distance L returns to a value coincident with the designated distance L0. When the distance L has returned to a value coincident with the designated distance L0, the moving velocity Sx is changed to an initial value (step 10), and the rotating mechanism 60 and the coating mechanism 90 are controlled by the control unit 100 such that the rotational speed N and the ejection rate F will be equal to the values calculated according to the formulas (1) and (2) (step 11). Thereafter, the control returns to the step 1.

If the distance L is determined in the step 4 to be in excess of the preliminarily inputted designated distance L0, the moving velocity Sx of the coating section 94 is faster than the drying speed, and, accordingly, the movable base 91 of the coating mechanism 90 is controlled to decrease the moving velocity Sx (step 12). The extent in which the moving velocity Sx is decreased when the distance L exceeds the designated distance L0 is preliminarily inputted as a parameter.

Thereafter, the rotational speed N of the balloon 30 and the ejection rate F of the coating liquid R are calculated by the formula (1) and formula (2), and the rotating mechanism 60 and the coating mechanism 90 are controlled by the control unit 100 such that the rotational speed N and the ejection rate F will be equal to the calculated values (step 13). After the moving velocity Sx is changed, the distance L is calculated on the basis of the signal from the detection section 80 (step 14), and it is determined whether or not the distance L coincides with the designated distance L0 (step 16). Then, the steps 14 to 16 are repeated until the distance L returns to a value coincident with the designated value L0. When the distance L has returned to a value coincident with the designated distance L0, the moving velocity Sx is changed to an initial value (step 17), and the rotating mechanism 60 and the coating mechanism 90 are controlled by the control unit 100 such that the rotational speed N and the ejection rate F will be equal to the values calculated according to the formulas (1) and (2) (step 18). Thereafter, the control returns to the step 1.

Then, when the coating section 94 has moved to a position on the proximalmost side of an area where the coating layer 32 is formed on the balloon 30, namely, on the proximalmost side of the straight portion 31, the rotating mechanism 60 and the coating mechanism 90 are controlled by the control unit 100 to stop the rotation of the balloon 30 and the supply of the coating liquid R (step 2, 8, or 15). The thickness of the coating layer 32 is, for example, 1 μm to 50 μm, which is not limitative but may be appropriately set according to the size of the balloon 30, the kind of the drug, etc.

Thereafter, the balloon catheter 10 is dismounted from the balloon coating apparatus 50, and the coating of the balloon 30 is completed.

As described above, the balloon coating method according to this embodiment is a balloon coating method for forming a coating layer 32 on an outer surface of a balloon 30 of a balloon catheter 10, the method including: a coating step of moving a coating section 94 for applying a coating liquid R containing a drug relative to the balloon 30 in the direction of an axis X, while rotating the balloon 30 about the axis X of the balloon 30, thereby to apply the coating liquid R to an outer surface of the balloon 30; a detection step of detecting the distance L of a dried part B where the coating liquid R applied to the outer surface of the balloon 30 has been dried from the coating section 94; and a control step of controlling moving velocity Sx of the coating section 94 relative to the balloon 30 in such a manner that the distance L of the dried part B from the coating section 94 is maintained at a preliminarily set designated distance L0. Therefore, the distance L of the coating section 94 from the dried part B can be constantly maintained in the state of being spaced by an appropriate distance, desirable drying conditions can constantly be maintained appropriately, and a uniform coating layer 32 can be formed. The drug in the coating formed on the outer surface of the balloon 30 can assume different morphological forms such as crystalline form, amorphous form and mixed forms thereof. Even in the case where the drug assumes a crystalline form, there may exist a variety of morphological forms, which differ in crystal structure. The crystals and amorphous phases may be arranged regularly or may be arranged irregularly, in the coating layer 32. Such a morphological form of the drug is influenced by the length of time of volatilization of the volatile solvent and the ambient temperature. Since in the balloon coating method according to this embodiment the desirable drying conditions can be appropriately set as aforementioned, therefore, the morphological form of the drug contained in the coating layer 32 can be freely controlled.

In addition, in the control step, the rotational speed N of the balloon 30 and the ejection quantity F from the coating section 94 per unit time are controlled according to variation in the moving velocity Sx of the coating section 94 in such a manner that the coating quantity V of the coating liquid R applied to the outer surface of the balloon 30 per unit area will be equal to a preliminarily set value. For this reason, even when the moving velocity Sx varies, the coating quantity V of the coating liquid R per unit area can be made uniform, and the thickness of the coating layer 32 formed can be made uniform.

In addition, in the control step, the rotational speed N of the balloon 30 is controlled such as to be equal to a value (divided value) obtained by dividing the changed moving velocity Sx of the coating section 94 by the inside diameter D which is the coating width along the direction of the axis X by which the coating section 94 coats at a time. For this reason, the position on the balloon 30 where the coating liquid R is applied by the coating section 94 is moved by a length amount of the inside diameter D per one revolution of the balloon 30, so that two-time coating of the balloon 30 does not occur, and a gap is not generated between portions of the coating liquid R applied in a spiral pattern. Accordingly, the coating liquid R can be applied without wasting the coating liquid R and in a uniform thickness.

In addition, in the detection step, the position of the dried part B on the outer surface of the balloon 30 is detected from a radially outer side of the balloon 30. Therefore, the distance L of the dried part B from the coating section 94 can be calculated. Note that the expression "from a radially outer side of the balloon 30" means a direction from an outer side than the balloon 30 toward the balloon 30, in a radial direction of the balloon 30. In this case, the angle of this direction relative to the outer surface of the balloon 30 is not limited; therefore, this direction may not necessarily be perpendicular to the outer surface of the balloon 30.

In addition, when a sensor for detection of transmittance of light is used as the detection section 80, the dried part B can be easily identified by utilizing the transmittance that changes due to the dried part B of the coating liquid R.

In addition, when a color difference meter is used as the detection section 80, the dried part B can be easily identified by utilizing the color that changes due to the dried part B of the coating liquid R.

A balloon coating method according to a second embodiment of the present disclosure differs from the first embodiment only in that a detection section 110 moved together with a coating section 94 is used. Note that the parts having the same or equivalent functions to those in the first embodiment are denoted by the same reference symbols as used above, and descriptions of these parts will be omitted.

Figure 5:
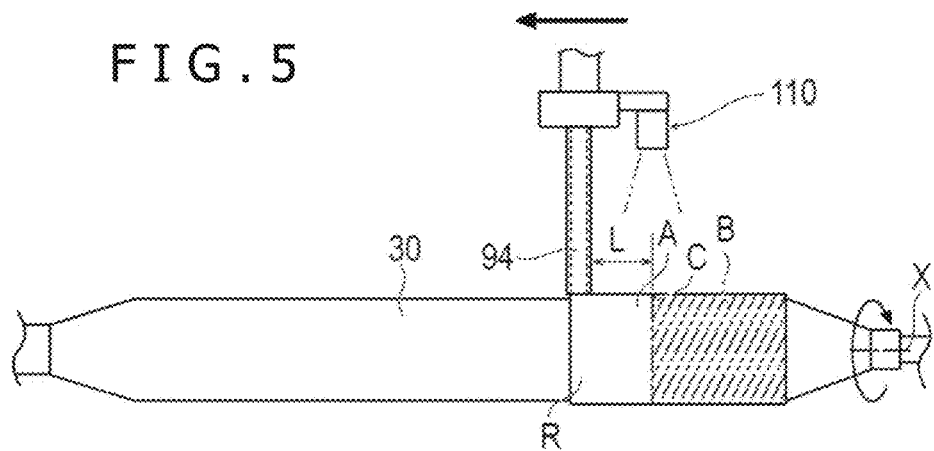
FIG. 5 is a schematic view showing an apparatus for carrying out a balloon coating method according to a second embodiment.

As shown in FIG. 5, the detection section 110 is fixed to the coating section 94 (or a movable base 91) in such a manner as to be movable together with the coating section 94. The detection section 110 detects a dried part B where a coating liquid R applied to an outer surface of a balloon 30 has been dried and a drug has been precipitated, through volatilization of the solvent of the coating liquid R. The detection by the detection section 110 may not necessarily cover the whole part of the range of coating of the balloon 30, and it is sufficient that the detection can cover a range including a position spaced distally from the coating section 94 by a designated distance L0. The detection section 110 is connected to a control unit 100, and transmits a detection signal to the control unit 100. For example, a transmittance measuring sensor based on laser light, a color difference meter, a camera can be applied to the detection section 110, like in the first embodiment.

Figure 6:
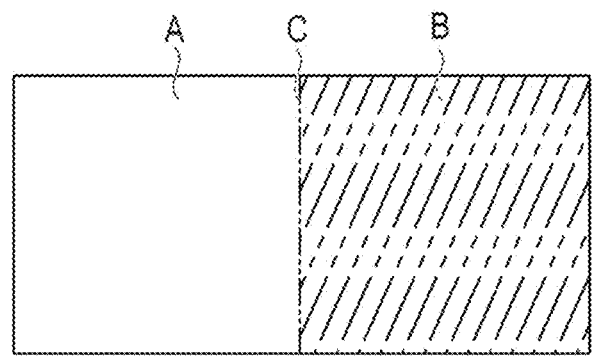
FIG. 6 is a view showing the results of detection by a detection section in the balloon coating method according to the second embodiment.

In a detection step in the second embodiment, the detection section 110 is moved together with the coating section 94. Therefore, as shown in FIG. 6, the ratio between the area (or the length along the direction of an axis X) of an undried part A where the coating liquid R has not yet been dried and the area (or the length along the direction of the axis X) of the dried part B where the coating liquid R has been dried is kept constant, unless the distance L from the coating section 94 to the dried part B is varied. For instance, a setting is made such that the distance L is equal to the designated distance L0 when the ratio is 1:1, and a variation in the ratio is calculated by the control unit 100 on the basis of a detection signal from the detection section 110. By such an operation, it is possible to determine whether the distance L is coincident with the designated distance L0, is less than the designated distance L0, or is in excess of the designated distance L0. Note that other steps are the same as in the first embodiment, and descriptions of the other steps are omitted.

As described above, in the balloon coating method according to the second embodiment, the position of the dried part B on the balloon 30 is detected from a radially outer side of the balloon 30 by use of the detection section 110 moved together with the coating section 94 in the detection step. Therefore, the distance L from the coating section 94 to the dried part B can be detected directly, without taking into account the movement of the coating section 94, so that the distance L can be calculated relatively easily and accurately.

A balloon coating method according to a third embodiment of the present disclosure differs from the first embodiment only in that a detection section 120 moved together with a coating section 94 is used. Note that the parts which have the same or equivalent functions to those in the first embodiment are denoted by the same reference symbols as used above, and descriptions of these parts will be omitted.

Figure 7:
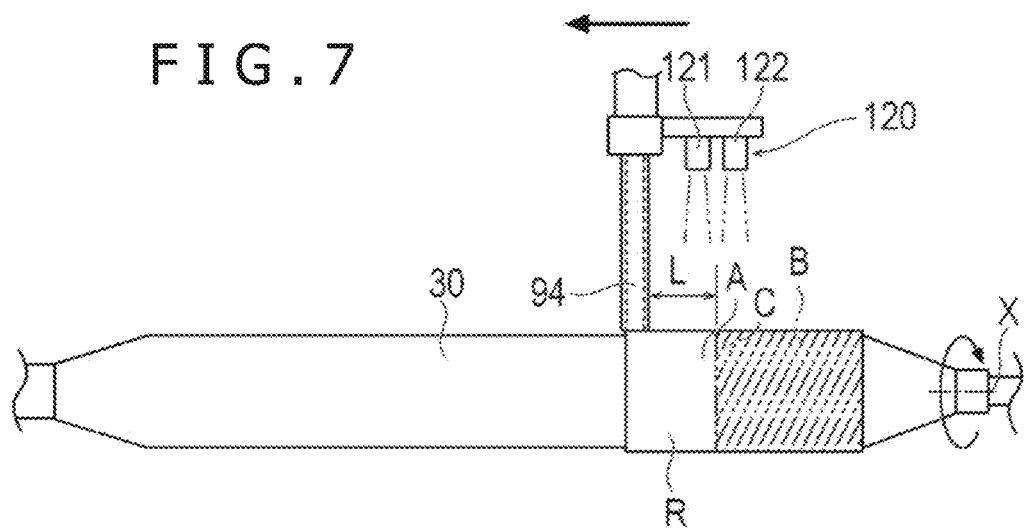
FIG. 7 is a schematic view showing an apparatus for carrying out a balloon coating method according to a third embodiment.

As shown in FIG. 7, the detection section 120 can include a first detection part 121 capable of detecting an undried part A where a coating liquid R has not been dried at or above a predetermined concentration on a side nearer to the coating section 94 than a reference position located at a designated distance L0 from the coating section 94, and a second detection part 122 capable of detecting a dried part B where the coating liquid R has been dried on a side farther from the coating section 94 than the reference position.

The first detection part 121 and the second detection part 122 are fixed to the coating section 94 (or a movable base 91) in such a manner as to be movable together with the coating section 94. The first detection part 121 and the second detection part 122 can be connected to a control unit 100, and transmit detection signals to the control unit 100. For example, a transmittance measuring sensor based on laser light, a color difference meter, or a camera can be applied to the first detection part 121 and the second detection part 122, like in the first embodiment.

In the case where the undried part A is detected by the first detection part 121 and the dried part B is detected by the second detection part 122 by a detection step in the third embodiment, it is determined by the control unit 100 that the distance L coincides with the designated distance L0. In this case, it can be determined that moving velocity Sx and drying speed are kept appropriate, and the moving velocity Sx is maintained unchanged in a control step.

In addition, in the case where the undried part A is detected by the first detection part 121 and where the dried part B is not detected by the second detection part 122, it is determined by the control unit 100 that the distance L is in excess of the designated distance L0. In this case, the moving velocity Sx is too fast as compared with the drying speed, and, accordingly, the moving velocity Sx is decreased in the control step.

In addition, in the case where the undried part A is not detected by the first detection part 121 and where the dried part B is detected by the second detection part 122, it is determined by the control unit 100 that the distance L is less than the designated distance L0. In this case, the moving velocity Sx is too slow as compared with the drying speed, and, accordingly, the moving velocity Sx is increased in the control step.

As described above, according to the third embodiment, the distance L from the coating section 94 to the dried part B can be detected by only determining whether or not a part under consideration is the undried part A by the first detection part 121 and determining whether or not a part under consideration is the dried part B by the second detection part 122, with the first detection part 121 and the second detection part 122 being moved together with the coating section 94. Therefore, an easier control can be realized. Note that other steps are the same as in the first embodiment, and, accordingly, descriptions of the other steps are omitted.

A balloon coating method according to a fourth embodiment of the present disclosure differs from the first embodiment only in that a balloon 30 is coated with a coating liquid R multiple times by a coating section 94.

In the balloon coating method according to the fourth embodiment, the rotational speed N (rpm) of the balloon 30 is calculated by using the following formula (3) in place of the formula (1) shown in the first embodiment. Specifically, the rotational speed N (rpm) of the balloon 30 is calculated by a control unit 100 by using the moving velocity Sx (mm/minute) of the coating section 94, the inside diameter D (mm) of a dispensing tube, and an overlap number i (times) which is the number of times of coating in multiple-time coating. The overlap number i is preliminarily set and inputted to the control unit 100. At the time of calculating the rotational speed N, in the same manner as in the first embodiment, a designated distance L0 as a range for the distance between a dried part B and the coating section 94 is preliminarily set and inputted, and the moving velocity Sx of the coating section 94 relative to the balloon 30 is controlled by the control unit 100 in such a manner that the distance L of the dried part B from the coating section 94 that is calculated from a signal received from a detection section 80 will be equal to the designated distance L0. Note that the method for controlling the moving velocity Sx may be the method shown in the second embodiment or the method shown in the third embodiment. Then, a rotating mechanism 60 is controlled by the control unit 100 in such a manner that the rotational speed N will be equal to the value calculated by the formula (3).

$$N = (Sx/D) \times i \qquad \text{Formula (3)}$$

With the formula (3) satisfied, a part corresponding to the inside diameter D of the coating section 94 passes the same part of the balloon 30 the overlap number i times, whereby the balloon 30 is coated with the coating liquid R multiple times in an overlapping manner. By coating multiple times in an overlapping manner, the coating liquid R can be gradually applied bit by bit, so that the coating liquid R can be uniformly applied while suppressing variability of the thickness of the coating liquid R applied.

Then, the ejection rate F (μL/minute) of the coating liquid R from the coating section 94 is calculated by the control unit 100 from the coating quantity V (μL/mm2) of the coating liquid R applied to an outer surface of the balloon 30 per unit area, the radius r (mm) of the balloon 30, the rotational speed N (rpm) calculated by the formula (3), the inside diameter D (mm) of the dispensing tube, and the overlap number i (times) by using the following formula (4). In addition, a coating mechanism 90 is controlled by the control unit 100 in such a manner that the ejection rate F will be equal to the value calculated in this manner. Note that the coating quantity V is not the quantity of the coating liquid R applied per one time in the overlap number i of times but is the final coating quantity of the coating liquid R applied the overlap number i of times.

$$F = V \times (2\pi \times r \times N)/i \times D \qquad \text{Formula (4)}$$

With the ejection rate F controlled in such a manner as to satisfy the formula (4), the coating quantity V preliminarily set as a desired coating quantity on the balloon 30 is maintained while performing multiple-time coating of the balloon 30 with the coating liquid R.

By controlling the rotational speed N and the ejection rate F such as to satisfy the formula (3) and the formula (4), as aforementioned, it is possible to suppress variability of the thickness of the coating liquid R and to make uniform the thickness of the coating layer 32 formed.

The present disclosure is not limited to the aforementioned embodiments, and various modifications can be made by one skilled in the art within the scope of the technical thought of the present disclosure. For instance, while coating with the coating liquid R is conducted gradually from the distal side of the balloon 30 in the aforementioned first to fourth embodiments, the coating may be conducted gradually from the proximal side.

In addition, while the coating section 94 is moved relative to the balloon 30 in the aforementioned embodiments, the balloon 30 may be moved relative to the coating section 94.

Figure 8:
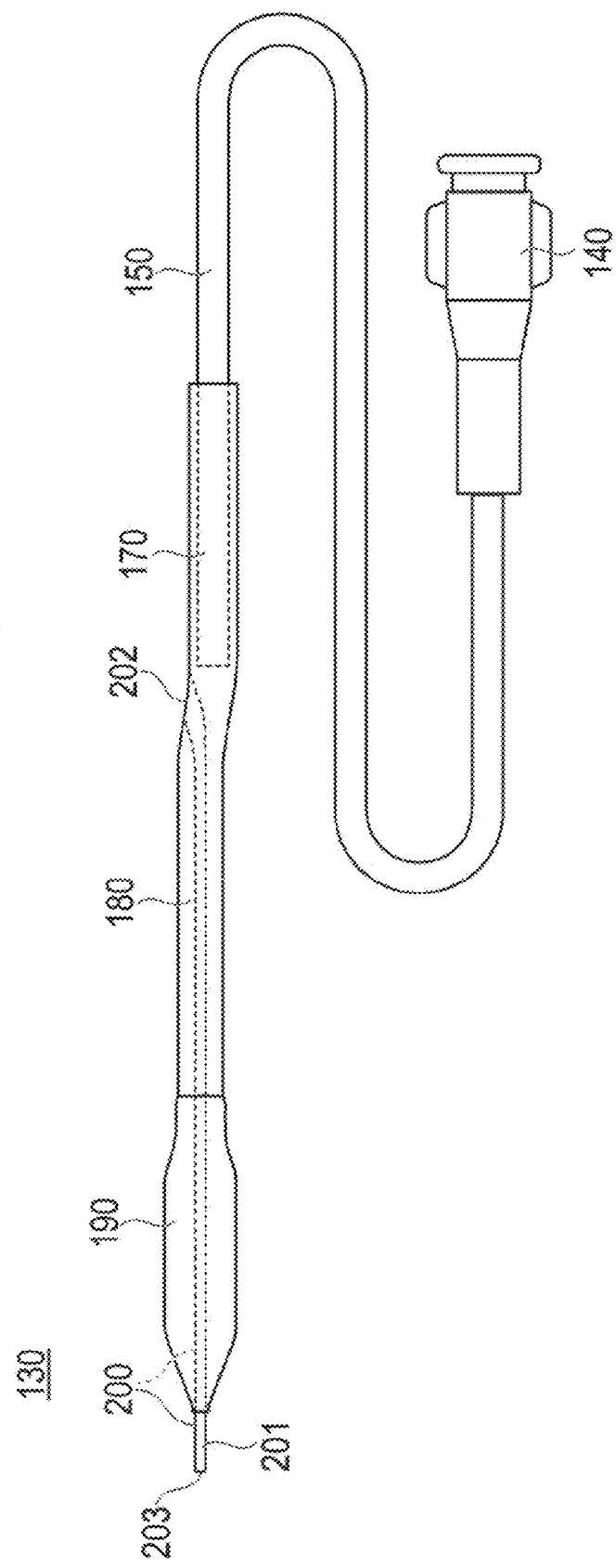
FIG. 8 is a plan view showing another example of the balloon catheter.
Figure 9:
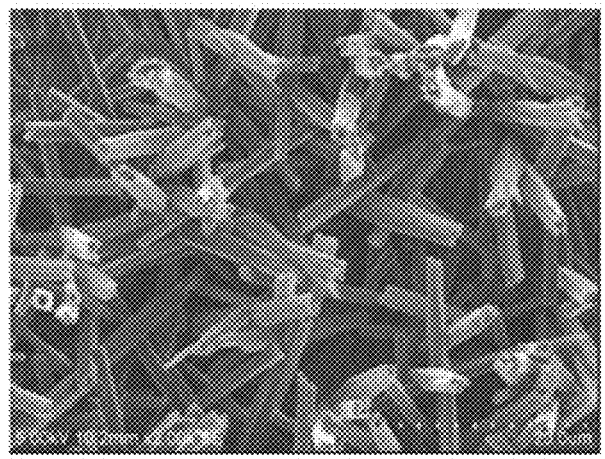
FIG. 9 is an illustration showing an SEM image with a magnification of 2,000× of crystals observed at a substrate surface of a coating layer formed in Example 1.
Figure 10:
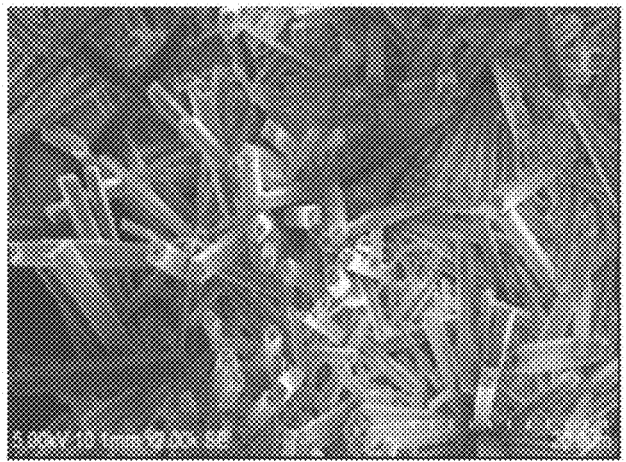
FIG. 10 is an illustration showing an SEM image with a magnification of 2,000× of crystals observed at a substrate surface of a coating layer formed in Example 2.
Figure 11:
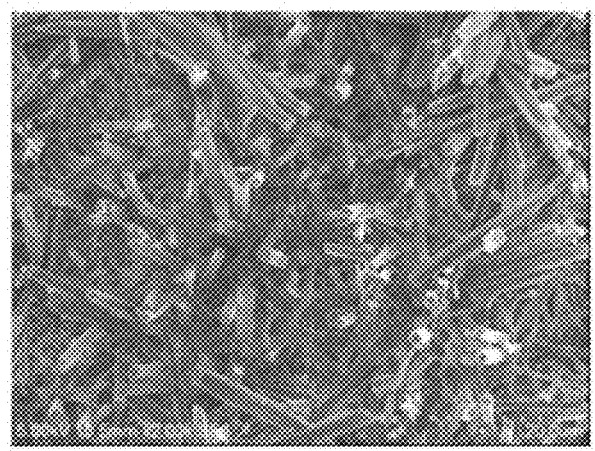
FIG. 11 is an illustration a drawing showing an SEM image with a magnification of 2,000× of crystals observed at a substrate surface of a coating layer formed in Example 3.
Figure 12:
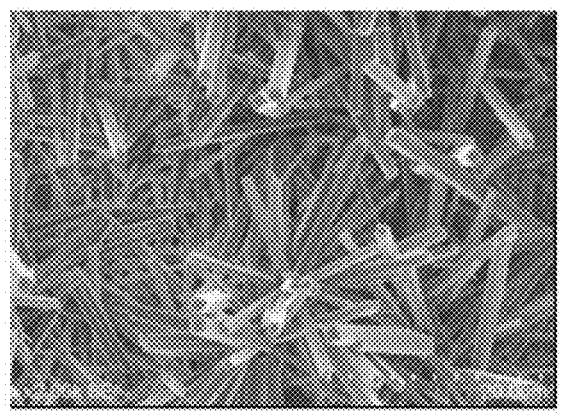
FIG. 12 is an illustration showing an SEM image with a magnification of 2,000× of crystals observed at a substrate surface of a coating layer formed in Example 4.
Figure 13:
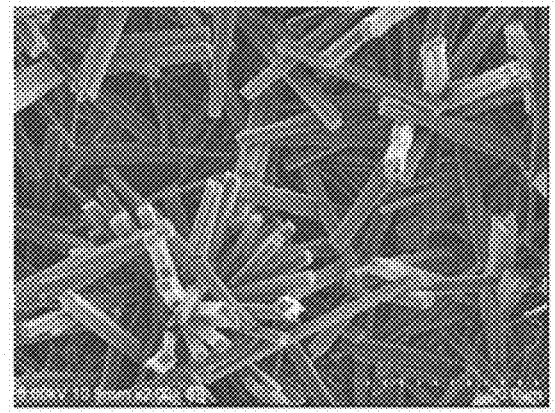
FIG. 13 is an illustration showing an SEM image with a magnification of 2,000× of crystals observed at a substrate surface of a coating layer formed in Example 5.
Figure 14:
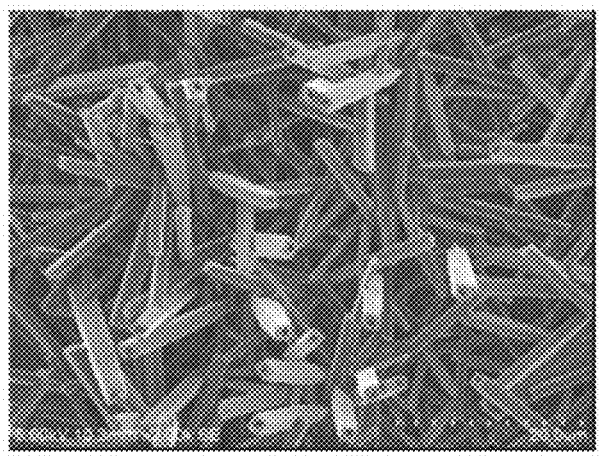
FIG. 14 is an illustration showing an SEM image with a magnification of 2,000× of crystals observed at a substrate surface of a coating layer formed in Example 6.
Figure 15:
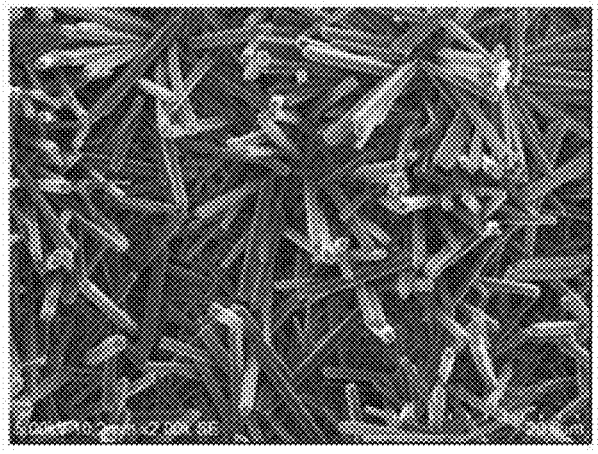
FIG. 15 is an illustration showing an SEM image with a magnification of 2,000× of crystals observed at a substrate surface of a coating layer formed in Example 7.
Figure 16:
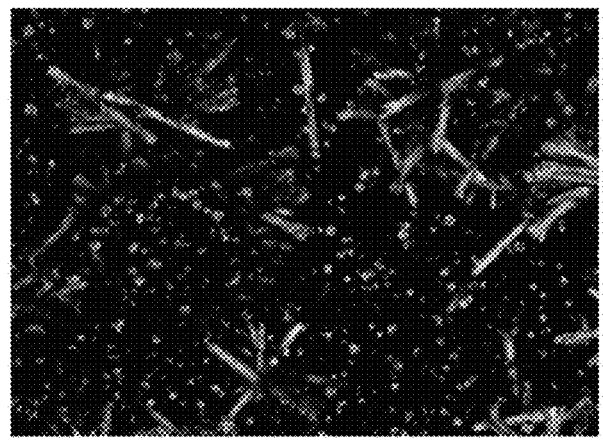
FIG. 16 is an illustration showing a laser microphotograph with a magnification of 2,000× of crystals observed at a substrate surface of a coating layer formed in Example 8.
Figure 17:
FIG. 17 is an illustration showing a laser microphotograph with a magnification of 2,000× of crystals observed at a substrate surface of a coating layer formed in Example 9.
Figure 18:
FIG. 18 is an illustration showing a laser microphotograph with a magnification of 2,000× of crystals observed at a substrate surface of a coating layer formed in Example 10.
Figure 19:
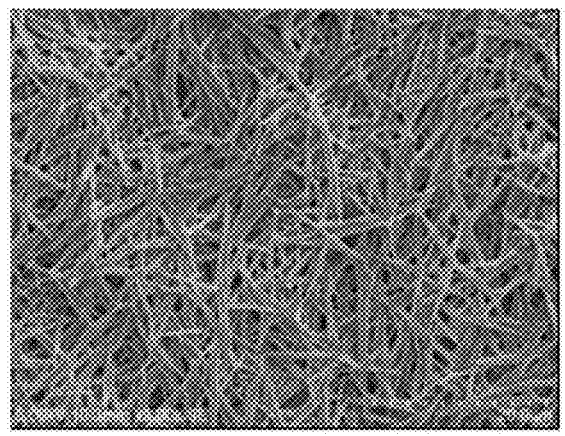
FIG. 19 is an illustration showing an SEM image with a magnification of 2,000× of crystals observed at a substrate surface of a coating layer formed in Example 11.
Figure 20:
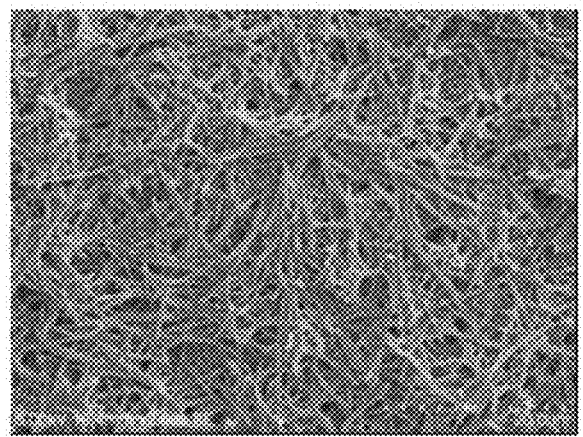
FIG. 20 is an illustration showing an SEM image with a magnification of 2,000× of crystals observed at a substrate surface of a coating layer formed in Example 12.
Figure 21:
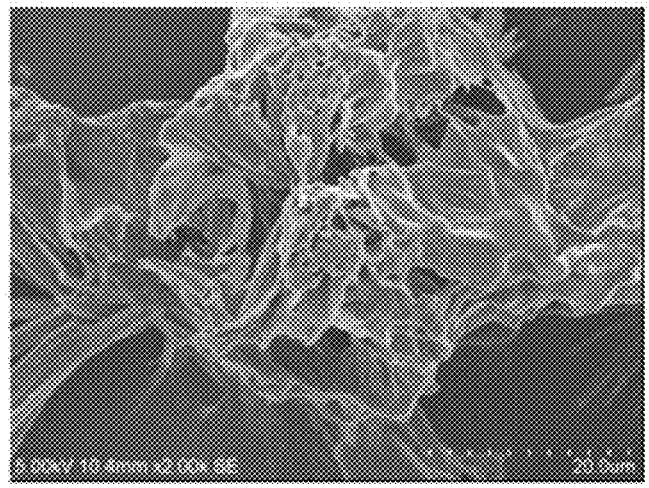
FIG. 21 is an illustration showing an SEM image with a magnification of 2,000× of crystals observed at a substrate surface of a coating layer formed in Example 13.
Figure 22:
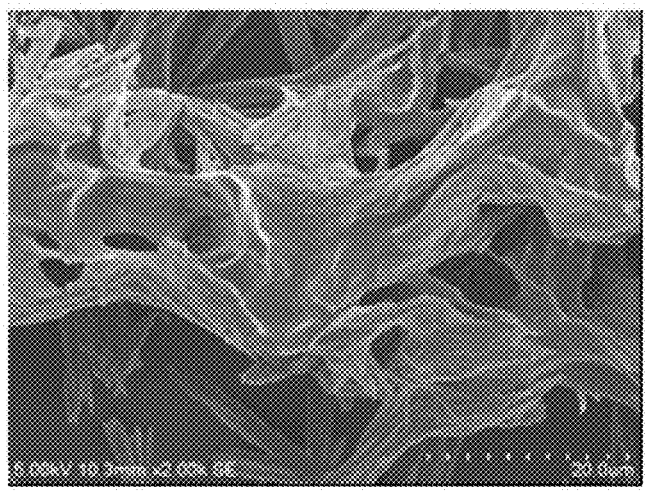
FIG. 22 is an illustration showing an SEM image with a magnification of 2,000× of crystals observed at a substrate surface of a coating layer formed in Example 14.
Figure 23:
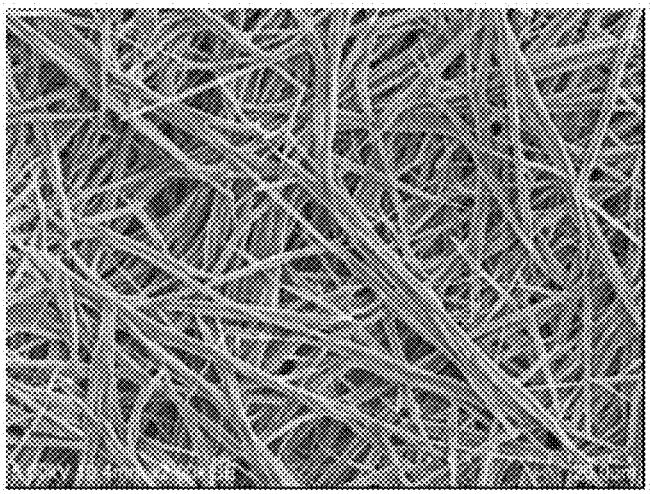
FIG. 23 is an illustration showing an SEM image with a magnification of 2,000× of crystals observed at a substrate surface of a coating layer formed in Example 15.
Figure 24:
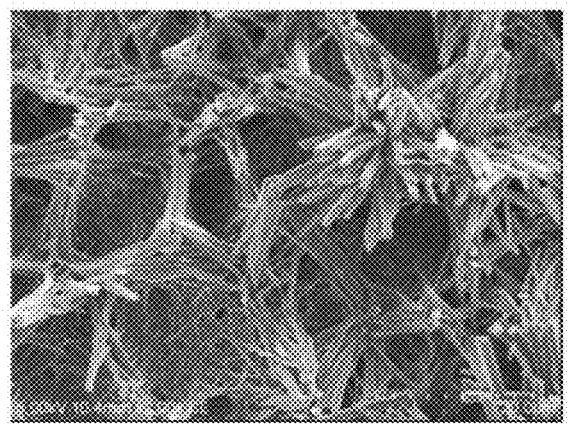
FIG. 24 is an illustration showing an SEM image with a magnification of 2,000× of crystals observed at a substrate surface of a coating layer formed in Example 16.

In addition, while the balloon 30 of an over-the-wire type balloon catheter 10 is coated in the balloon coating methods according to the aforementioned embodiments, a balloon 190 of a rapid change type balloon catheter 130 as shown in FIG. 8 may be coated. The balloon catheter 130 can include a hub 140, a proximal shaft 150, an intermediate portion 170, a distal shaft 180, the balloon 190, and an inner tube shaft 200, from the proximal side.

To the hub 140, the proximal shaft 150 formed of a material having a comparatively high rigidity such as metals and some of resins is joined in such communication that fluid can flow therethrough.

On the distal side of the proximal shaft 150, the intermediate portion 170 is provided in such communication that fluid can flow therethrough. On the distal side of the intermediate portion 170, the distal shaft 180 formed of such a material as resin and having a comparatively low rigidity is provided in such communication that fluid can flow therethrough. On the distal side of the distal shaft 180, a proximal portion of the balloon 190 is provided in such communication that fluid can flow therethrough.

The inner tube shaft 200 coaxially penetrates the inside of the distal shaft 180 and the balloon 190. A distal portion of the inner tube shaft 200 constitutes a tip 201, which extends distally beyond a distal portion of the balloon 190. The tip 201 is joined to the distal portion of the balloon 190 in a liquid-tight state. A proximal end of the inner tube shaft 200 is extended to a guide wire opening portion 202 provided at part of a portion ranging from the intermediate portion 170 to the distal shaft 180, and is joined to the guide wire opening portion 202 in a liquid-tight manner. A guide wire can be inserted into the inner tube shaft 200, with a distal opening portion 203 of the tip 201 as an entrance and with the guide wire opening portion 202 as an exit.

Even the balloon catheter 130 of the rapid exchange type aforementioned can be mounted to the balloon coating apparatus 50 by a method wherein the balloon 190 is inflated and sealed, the hub 140 is attached to the rotating mechanism 60, at least part of the proximal shaft 150, the intermediate portion 170 and the distal shaft 180 is supported by a support base 70, and a core member 61 is inserted into the inner tube shaft 200 via the guide wire opening portion 202. Then, a coating layer can be formed on an outer surface of the balloon 190 by a method, which is the same or equivalent to the methods described in the first to fourth embodiments.

The present disclosure will be described below referring to Examples and Comparative Examples, but the disclosure is not limited to these Examples.

Example 1

(1) Preparation of Coating Solution 1

70 mg of L-serine ethyl ester hydrochloride (CAS No. 26348-61-8) and 180 mg of paclitaxel (CAS No. 33069-62-4) were weighed. To these were added 1.4 mL of anhydrous ethanol, 2.0 mL of acetone, 0.5 mL of tetrahydrofuran, and 1.1 mL of RO (Reverse Osmosis, or reverse osmosis membrane)-treated water (hereinafter referred to as RO water) to allow dissolution, thereby preparing coating solution 1.

(2) Coating of Balloon with Drug

A balloon catheter balloon having an inflatable portion sized to be 7.0 mm in diameter and 120 mm in length when inflated (the inflatable portion made of nylon 12) was prepared. The balloon in an inflated state was coated with the coating solution such that the solvent volatilized slowly and the quantity of paclitaxel would be approximately 3 μg/mm2. Specifically, while a side surface of the distal end of a dispensing tube (coating section) for ejecting the drug was constantly kept in contact with the catheter surface, the drug was ejected from a distal opening of the dispensing tube. The balloon catheter was rotated about its long axis in the direction opposite (reverse) to the drug ejecting direction. The moving velocity of the dispensing tube in the axial direction of the balloon catheter and the rotational speed of the balloon were controlled, and, simultaneously with the rotation, the drug was ejected at a rate of 0.897 μL/second, to perform coating. At the time of coating, an undried distance control value as a set point and an allowable fluctuation range in absolute value were set, the width of an undried part was controlled while monitoring the undried part by use of a camera, and the width of the undried part was measured in an initial period, a middle period and a later period of coating. Thereafter, the coated balloon was dried, to produce a drug eluting balloon in Example 1. A designated distance for controlling the distance of the dried part from the dispensing tube (the width of the undried part) was 7 mm to 19 mm (the undried distance control value=13 mm and the absolute value of the allowable fluctuation range≤6 mm). The width of the undried part was 13 mm in the initial period of the coating treatment, 13 mm in the middle period of the coating treatment, and 13 mm in the later period of the coating treatment.

Example 2

A drug eluting balloon in Example 2 was produced by setting the drug ejection rate to 0.718 μL/second and setting the other conditions in the same manner as in Example 1. The designated distance for controlling the width of the undried part was 4 mm to 16 mm (the undried distance control value=10 mm and the absolute value of the allowable fluctuation range≤6 mm). The width of the undried part was 10 mm in the initial period the coating treatment, 10 mm in the middle period, and 9 mm in the later period.

Example 3

A drug eluting balloon in Example 3 was produced by setting the drug ejection rate to 0.538 μL/second and setting the other conditions in the same manner as in Example 1. The designated distance for controlling the width of the undried part was 2 mm to 14 mm (the undried distance control value=8 mm and the absolute value of the allowable fluctuation range≤6 mm). The width of the undried part was 8 mm in the initial period of the coating treatment, 8 mm in the middle period, and 7 mm in the later period.

Example 4

A drug eluting balloon in Example 4 was produced by setting the drug ejection rate to 0.359 μL/second and setting the other conditions in the same manner as in Example 1. The designated distance for controlling the width of the undried part was 2 mm to 14 mm (the undried distance control value=8 mm and the absolute value of the allowable fluctuation range≤6 mm). The width of the undried part was 4 mm in the initial period of the coating treatment, 3 mm in the middle period, and 2 mm in the later period.

Example 5

(1) Preparation of Coating Solution 2

70 mg of L-serine ethyl ester hydrochloride (CAS No. 26348-61-8) and 180 mg of paclitaxel (CAS No. 33069-62-4) were weighed. To these were added 1.5 mL of anhydrous ethanol, 2.0 mL of acetone, 0.5 mL of tetrahydrofuran, and 1 mL of RO water to allow dissolution, thereby preparing coating solution 2.

(2) Coating of Balloon with Drug

A balloon catheter balloon having an inflatable portion sized to be 7.0 mm in diameter and 120 mm in length when inflated (the inflatable portion made of nylon 12) was prepared. The balloon in an inflated state was coated with the coating solution such that the solvent volatilized slowly and the quantity of paclitaxel would be approximately 3 μg/mm2. Specifically, while a side surface of the distal end of a dispensing tube (coating section) for ejecting the drug was constantly kept in contact with the catheter surface, the drug was ejected from a distal opening of the dispensing tube. The balloon catheter was rotated about its long axis in the direction opposite (reverse) to the drug ejecting direction. The moving velocity of the dispensing tube in the axial direction of the balloon catheter and the rotational speed of the balloon were controlled, and, simultaneously with the rotation, the drug was ejected at a rate of 0.359 μL/second, to perform coating. At the time of coating, an undried distance control value as a set point and an allowable fluctuation range in absolute value were set, the width of an undried part was controlled while monitoring the undried part by use of a camera, and the width of the undried part was measured in an initial period, a middle period and a later period of coating. Thereafter, the coated balloon was dried, to produce a drug eluting balloon. A designated distance for controlling the distance of the dried part from the dispensing tube (the width of the undried part) was 0 mm to 12 mm (the undried distance control value=6 mm and the absolute value of the allowable fluctuation range≤6 mm). The width of the undried part was 6 mm in the initial period of the coating treatment, 5 mm in the middle period of the coating treatment, and 6 mm in the later period of the coating treatment.

Example 6

A drug eluting balloon in Example 6 was produced by setting the drug ejection rate to 0.479 μL/second, setting the size of the inflatable portion of the balloon to be 7.0 mm in diameter and 80 mm in length when inflated, and setting the other conditions in the same manner as in Example 1. The designated distance for controlling the width of the undried part was 7 mm to 19 mm (the undried distance control value=13 mm and the absolute value of the allowable fluctuation range≤6 mm). The width of the undried part was 13 mm in the initial period of the coating treatment, 8 mm in the middle period, and 9 mm in the later period.

Example 7

A drug eluting balloon in Example 7 was produced by setting the drug ejection rate to 0.240 μL/second, setting the size of the inflatable portion of the balloon to be 7.0 mm in diameter and 80 mm in length when inflated, and setting the other conditions in the same manner as in Example 5. The designated distance for controlling the width of the undried part was 1 mm to 13 mm (the undried distance control value=7 mm and the absolute value of the allowable fluctuation range≤6 mm). The width of the undried part was 7 mm in the initial period of the coating treatment, 4 mm in the middle period, and 4 mm in the later period.

Example 8

A drug eluting balloon in Example 8 was produced by setting the drug ejection rate to 0.240 μL/second, setting the size of the inflatable portion of the balloon to be 2.0 mm in diameter and 200 mm in length when inflated, and setting the other conditions in the same manner as in Example 1. The designated distance for controlling the width of the undried part was 2 mm to 12 mm (the undried distance control value=7 mm and the absolute value of the allowable fluctuation range≤5 mm). The width of the undried part was 7 mm in the middle period of the coating treatment.

Example 9

A drug eluting balloon in Example 9 was produced by setting the drug ejection rate to 0.204 μL/second, setting the size of the inflatable portion of the balloon to be 2.0 mm in diameter and 200 mm in length when inflated, and setting the other conditions in the same manner as in Example 1. The designated distance for controlling the width of the undried part was 1 mm to 11 mm (the undried distance control value=6 mm and the absolute value of the allowable fluctuation range≤5 mm). The width of the undried part was 6 mm in the middle period of the coating treatment.

Example 10

A drug eluting balloon in Example 10 was produced by setting the drug ejection rate to 0.168 μL/second, setting the size of the inflatable portion of the balloon to be 2.0 mm in diameter and 200 mm in length when inflated, and setting the other conditions in the same manner as in Example 1. The designated distance for controlling the width of the undried part was 0 mm to 10 mm (the undried distance control value=5 mm and the absolute value of the allowable fluctuation range≤5 mm). The width of the undried part was 4 mm in the middle period of the coating treatment.

Example 11

A drug eluting balloon in Example 11 was produced by setting the drug ejection rate to 0.179 μL/second and setting the other conditions in the same manner as in Example 5. The designated distance for controlling the width of the undried part was 0 mm to 4 mm (the undried distance control value=2 mm and the absolute value of the allowable fluctuation range≤2 mm). The width of the undried part was 2 mm in the initial period of the coating treatment, 1 mm in the middle period, and 0 mm in the later period.

Example 12

A drug eluting balloon in Example 12 was produced by setting the drug ejection rate to 0.090 μL/second and setting the other conditions in the same manner as in Example 5. The designated distance for controlling the width of the undried part was 0 mm (the undried distance control value=0 mm and the absolute value of the allowable fluctuation range≤0 mm). The width of the undried part was 0 mm in the initial period of the coating treatment, 0 mm in the middle period, and 0 mm in the later period.

Example 13

A drug eluting balloon in Example 13 was produced by setting the drug ejection rate to 0.957 μL/second, setting the size of the inflatable portion of the balloon to be 4.0 mm in diameter and 80 mm in length when inflated, and setting the other conditions in the same manner as in Example 1. The designated distance for controlling the width of the undried part was 14 mm to 26 mm (the undried distance control value=20 mm and the absolute value of the allowable fluctuation range≤6 mm). The width of the undried part was 19 mm in the initial period of the coating treatment, 19 mm in the middle period, and 19 mm in the later period.

Example 14

A drug eluting balloon in Example 14 was produced by setting the drug ejection rate to 0.719 μL/second, setting the size of the inflatable portion of the balloon to be 4.0 mm in diameter and 80 mm in length when inflated, and setting the other conditions in the same manner as in Example 1. The designated distance for controlling the width of the undried part was 13 mm to 25 mm (the undried distance control value=19 mm and the absolute value of the allowable fluctuation range≤6 mm). The width of the undried part was 19 mm in the initial period of the coating treatment, 17 mm in the middle period, and 13 mm in the later period.

Example 15

A drug eluting balloon in Example 15 was produced by setting the drug ejection rate to 0.240 μL/second, setting the size of the inflatable portion of the balloon to be 4.0 mm in diameter and 80 mm in length when inflated, and setting the other conditions in the same manner as in Example 1. The designated distance for controlling the width of the undried part was 0 mm (the undried distance control value=0 mm and the absolute value of the allowable fluctuation range≤0 mm). The width of the undried part was 0 mm in the initial period of the coating treatment, 0 mm in the middle period, and 0 mm in the later period.

Example 16

A drug eluting balloon in Example 16 was produced by setting the drug ejection rate to 0.120 µL/second, setting the size of the inflatable portion of the balloon to be 4.0 mm in diameter and 80 mm in length when inflated, and setting the other conditions in the same manner as in Example 5. The designated distance for controlling the width of the undried part was 0 mm (the undried distance control value=0 mm and the absolute value of the allowable fluctuation range≤0 mm). The width of the undried part was 0 mm in the initial period of the coating treatment, 0 mm in the middle period, and 0 mm in the later period.

Comparative Example 1

A drug eluting balloon in Comparative Example 1 was produced by setting the drug ejection rate to 1.436 µL/second and setting the other conditions in the same manner as in Example 1. Note that a control of the moving velocity of the dispensing tube relative to the balloon such that the width of the undried part would be within a preliminarily set designated distance was not conducted. The width of the undried part was 30 mm in the initial period of the coating treatment, 25 mm in the middle period, and 22 mm in the later period.

Comparative Example 2

A drug eluting balloon in Comparative Example 2 was produced by setting the drug ejection rate to 1.256 µL/second and setting the other conditions in the same manner as in Example 1. Note that a control of the moving velocity of the dispensing tube relative to the balloon such that the width of the undried part would be within a preliminarily set designated distance was not performed. The width of the undried part was 27 mm in the initial period of the coating treatment, 22 mm in the middle period, and 20 mm in the later period.

[Observation of Coating Layer of Drug Eluting Balloon Under Scanning Electron Microscope (SEM)]

Figure 25:
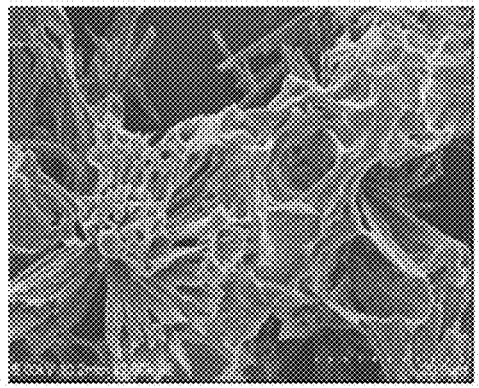
FIG. 25 is an illustration showing an SEM image with a magnification of 2,000× of crystals observed at a substrate surface of a coating layer formed in Comparative Example 1.
Figure 26:
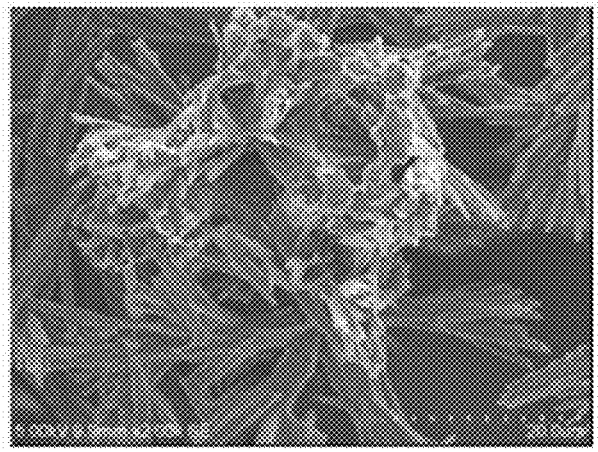
FIG. 26 is an illustration showing an SEM image with a magnification of 2,000× of crystals observed at a substrate surface of a coating layer formed in Comparative Example 2.

Table 1 shows conditions and measured values of the width of the undried part, for Examples and Comparative Examples. The drug eluting balloons of Examples 1 to 16 and Comparative Examples 1 and 2 were each dried, cut to an appropriate size, the cut piece was placed on a support base, and platinum was vapor deposited thereon from above. The surface and the inside of the coat layer of each sample after the platinum vapor deposition were observed under a scanning electron microscope (SEM). Microphotographs obtained for Examples 1 to 16 are shown in FIGS. 9 to 24, and microphotographs obtained for Comparative Examples 1 and 2 are shown in FIGS. 25 and 26. As a result, it was confirmed that by controlling the moving velocity of the dispensing tube relative to the balloon in such a manner that the distance of the dried part from the dispensing tube will be maintained at a preliminarily set designated distance, it is possible to set, for example, the thickness and/or morphological form of the drug in the coating formed on the balloon in a variety of manners and appropriately.

The detailed description above describes a balloon coating method and a balloon coating apparatus for forming a coating layer on a surface of a balloon. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

TABLE 1

| | Balloon size | Coating solution | Drug ejection rate (µL/second) | Undried distance control Value (mm) | Absolute value of allowable fluctuation range (mm) | Width of undried part (mm) | | |
|---|---|---|---|---|---|---|---|---|
| | | | | | | Initial period | Middle period | Later period |
| Example 1 | φ 7 mm/L 120 mm | 1 | 0.897 | 13 | ≤6 | 13 | 13 | 13 |
| Example 2 | φ 7 mm/L 120 mm | 1 | 0.718 | 10 | ≤6 | 10 | 10 | 9 |
| Example 3 | φ 7 mm/L 120 mm | 1 | 0.538 | 8 | ≤6 | 8 | 7 | 7 |
| Example 4 | φ 7 mm/L 120 mm | 1 | 0.359 | 4 | ≤6 | 4 | 3 | 2 |
| Example 5 | φ 7 mm/L 120 mm | 2 | 0.359 | 6 | ≤6 | 6 | 5 | 6 |
| Example 6 | φ 4 mm/L 80 mm | 1 | 0.479 | 13 | ≤6 | 13 | 8 | 9 |
| Example 7 | φ 4 mm/L 80 mm | 2 | 0.240 | 7 | ≤6 | 7 | 4 | 4 |
| Example 8 | φ 2 mm/L 200 mm | 1 | 0.240 | 7 | ≤5 | | 7 | |
| Example 9 | φ 2 mm/L 200 mm | 1 | 0.204 | 6 | ≤5 | | 6 | |
| Example 10 | φ 2 mm/L 200 mm | 1 | 0.168 | 5 | ≤5 | | 4 | |
| Example 11 | φ 7 mm/L 120 mm | 2 | 0.179 | 2 | ≤2 | 2 | 1 | 0 |
| Example 12 | φ 7 mm/L 120 mm | 2 | 0.090 | 0 | ≤0 | 0 | 0 | 0 |
| Example 13 | φ 4 mm/L 80 mm | 1 | 0.957 | 20 | ≤6 | 19 | 19 | 19 |
| Example 14 | φ 4 mm/L 80 mm | 1 | 0.719 | 19 | ≤6 | 19 | 17 | 13 |
| Example 15 | φ 4 mm/L 80 mm | 1 | 0.240 | 0 | ≤0 | 0 | 0 | 0 |
| Example 16 | φ 4 mm/L 80 mm | 2 | 0.120 | 0 | ≤0 | 0 | 0 | 0 |
| Comp. Ex. 1 | φ 7 mm/L 120 mm | 1 | 1.436 | | | 30 | 25 | 22 |
| Comp. Ex. 2 | φ 7 mm/L 120 mm | 1 | 1.256 | | | 27 | 22 | 20 |

What is claimed is:

1. A balloon coating method for forming a coating layer on an outer surface of a balloon of a balloon catheter, the method comprising:
   a coating step of moving a coating section relative to the balloon in an axial direction for applying a coating liquid containing a drug, while rotating the balloon about an axis of the balloon, thereby to apply the coating liquid to an outer surface of the balloon;

a detection step of detecting a distance of a dried part where the coating liquid applied to the outer surface of the balloon has been dried from the coating section;

a control step of controlling a moving velocity of the coating section relative to the balloon in such a manner that the distance of the dried part from the coating section is maintained at a preliminarily set designated distance;

wherein in the detection step, detection of an undried part where the coating liquid has not yet been dried is performed on a side nearer to the coating section than a reference position spaced by a designated distance from the coating section, by a first detection section moved together with the coating section;

whereas detection of the dried part is performed on a side farther from the coating section than the reference position, by a second detection section moved together with the coating section;

in the control step, the moving velocity of the coating section is not changed in a case where the undried part is detected by the first detection section and the dried part is detected by the second detection section;

the moving velocity of the coating section is increased in a case where the undried part is not detected by the first detection section; and the moving velocity of the coating section is lowered in a case where the dried part is not detected by the second detection section.

2. The balloon coating method according to claim 1, wherein in the control step, a rotational speed of the balloon and a quantity of the coating liquid ejected from the coating section per unit time are controlled according to variation in moving velocity of the coating section in such a manner that the quantity of the coating liquid applied to the balloon surface per unit time is equal to a preliminarily set value.

3. A balloon coating method for forming a coating layer on an outer surface of a balloon of a balloon catheter, the method comprising:

a coating step of moving a coating section relative to the balloon in an axial direction for applying a coating liquid containing a drug, while rotating the balloon about an axis of the balloon, thereby to apply the coating liquid to an outer surface of the balloon;

a detection step of detecting a distance of a dried part where the coating liquid applied to the outer surface of the balloon has been dried from the coating section;

a control step of controlling a moving velocity of the coating section relative to the balloon in such a manner that the distance of the dried part from the coating section is maintained at a preliminarily set designated distance; and wherein in the control step, a rotational speed of the balloon is controlled in such a manner that the rotational speed will be equal to a value obtained by dividing a changed moving velocity of the coating section by a coating width along the axial direction by which the coating liquid is applied at a time by the coating section.

4. The balloon coating method according to claim 1, wherein in the detection step, a position of the dried part on the outer surface of the balloon is detected from a radially outer side of the balloon.

5. The balloon coating method according to claim 1, wherein in the detection step, a position of the dried part on the outer surface of the balloon is detected from a radially outer side of the balloon by use of a detection section moved together with the coating section.

6. The balloon coating method according to claim 1, wherein in the detection step, a control is conducted such that the width along the axial direction of the undried part detected by a first detection section is in a range of 2 mm to 20 mm.

7. The balloon coating method according to claim 1, wherein in the detection step, a control is conducted such that the length from an allowable upper limit to an allowable lower limit of the width along the axial direction of the undried part detected by a first detection section is not more than 12 mm during a period from start of coating to end of coating.

8. The balloon coating method according to claim 1, comprising:

using a sensor for detecting transmittance of light as the detection section.

9. The balloon coating method according to claim 1, comprising:

using a color difference meter as the detection section.

10. A balloon coating method for forming a coating layer on an outer surface of a balloon of a balloon catheter, the method comprising:

rotating the balloon about an axis of the balloon;

applying a coating liquid containing a drug to an outer surface of the balloon by moving a coating section relative to the balloon in an axial direction;

detecting a distance of a dried part where the coating liquid applied to the outer surface of the balloon has been dried from the coating section;

controlling a moving velocity of the coating section relative to the balloon and maintaining the distance of the dried part from the coating section at a preliminarily set designated distance; and conducting a control such that the width along the axial direction of an undried part detected by a first detection section is in a range of 2 mm to 20 mm, or conducting a control such that the length from an allowable upper limit to an allowable lower limit of the width along the axial direction of the undried part detected by a first detection section is not more than 12 mm during a period from start of coating to end of coating.

11. The balloon coating method according to claim 10, comprising:

controlling a rotational speed of the balloon and a quantity of the coating liquid ejected from the coating section per unit time according to variation in moving velocity of the coating section in such a manner that the quantity of the coating liquid applied to the balloon surface per unit time is equal to a preliminarily set value.

12. The balloon coating method according to claim 10, comprising:

controlling a rotational speed of the balloon such that the rotational speed is equal to a value obtained by dividing a changed moving velocity of the coating section by a coating width along the axial direction by which the coating liquid is applied at a time by the coating section.

13. The balloon coating method according to claim 10, comprising:

detecting a position of the dried part on the outer surface of the balloon from a radially outer side of the balloon.

14. The balloon coating method according to claim 10, comprising:

detecting a position of the dried part on the outer surface of the balloon from a radially outer side of the balloon by use of a detection section moved together with the coating section.

15. The balloon coating method according to claim 10, comprising:
- detecting the undried part where the coating liquid has not yet been dried on a side nearer to the coating section than a reference position spaced by a designated distance from the coating section, by a first detection section moved together with the coating section;
- detecting the dried part on a side farther from the coating section than the reference position, by a second detection section moved together with the coating section;
- detecting the moving velocity of the coating section is not changed in a case where the undried part is detected by the first detection section and the dried part is detected by the second detection section;
- increasing the moving velocity of the coating section when the undried part is not detected by the first detection section; and
- reducing the moving velocity of the coating section in a case where the dried part is not detected by the second detection section.

16. The balloon coating method according to claim 10, comprising:
- using a sensor for detecting transmittance of light as the detection section.

17. The balloon coating method according to claim 10, comprising:
- using a color difference meter as the detection section.

* * * * *